(12) United States Patent
Ikari et al.

(10) Patent No.: US 10,524,940 B2
(45) Date of Patent: Jan. 7, 2020

(54) STENT

(71) Applicants: TOKAI UNIVERSITY EDUCATIONAL SYSTEM, Tokyo (JP); NIPRO CORPORATION, Osaka-shi, Osaka (JP)

(72) Inventors: Yuji Ikari, Isehara (JP); Kuniaki Matsumoto, Osaka (JP)

(73) Assignees: TOKAI UNIVERSITY EDUCATIONAL SYSTEM, Tokyo (JP); NIPRO CORPORATION, Osaka (JP)

( * ) Notice: Subject to any disclaimer, the term of this patent is extended or adjusted under 35 U.S.C. 154(b) by 137 days.

(21) Appl. No.: 14/787,972

(22) PCT Filed: May 12, 2014

(86) PCT No.: PCT/JP2014/062591
§ 371 (c)(1),
(2) Date: Oct. 29, 2015

(87) PCT Pub. No.: WO2014/188899
PCT Pub. Date: Nov. 27, 2014

(65) Prior Publication Data
US 2016/0106561 A1 Apr. 21, 2016

(30) Foreign Application Priority Data
May 23, 2013 (JP) .................................. 2013-108691

(51) Int. Cl.
*A61F 2/89* (2013.01)
*A61F 2/06* (2013.01)
(52) U.S. Cl.
CPC ..................................... *A61F 2/89* (2013.01)

(58) Field of Classification Search
CPC .......... A61F 2/915; A61F 2/07; A61F 2/2418; A61F 2002/91558; A61F 2002/91583; A61F 2002/9511; A61F 2/89; A61F 2/90
See application file for complete search history.

(56) References Cited

U.S. PATENT DOCUMENTS 5,449,373 A * 9/1995 Pinchasik ............... A61F 2/856
606/198
5,733,303 A * 3/1998 Israel ........................ A61F 2/91
623/1.15
(Continued)

FOREIGN PATENT DOCUMENTS

EP     1 523 959 A2    4/2005
JP     2007-500051 A    1/2007
(Continued)

OTHER PUBLICATIONS

Nov. 22, 2016 European Search Report issued in European Patent Application No. 14800612.5.
(Continued)

*Primary Examiner* — Ann Schillinger
(74) *Attorney, Agent, or Firm* — Oliff PLC

(57) ABSTRACT

Provided is a stent having a novel structure, the stem simultaneously having both the stability of shape against the action of external force, such as compression force, tensile force, or torsional force, and high flexibility in the direction of twisting of the stem. Connection groups are provided at three or more positions set at circumferentially equally-spaced intervals, the connection groups each including connection sections which are disposed circumferentially close to each other between axially adjacent tubular divided bodies. The connection groups on both sides axially of each of the tubular divided bodies are provided at positions (Continued)

circumferentially offset from each other while at least one turning portion is present between the connection groups.

12 Claims, 14 Drawing Sheets

(56) References Cited

U.S. PATENT DOCUMENTS

| | | | |
|---|---|---|---|
| 6,129,755 A | 10/2000 | Mathis et al. | |
| 6,596,021 B1* | 7/2003 | Lootz | A61F 2/91 623/1.16 |
| 2004/0243216 A1* | 12/2004 | Gregorich | A61F 2/91 623/1.15 |
| 2007/0021827 A1 | 1/2007 | Lowe et al. | |
| 2007/0050011 A1 | 3/2007 | Klein et al. | |
| 2010/0057190 A1 | 3/2010 | Issenmann | |
| 2010/0256739 A1 | 10/2010 | Tippett et al. | |
| 2010/0298921 A1 | 11/2010 | Schlun et al. | |

FOREIGN PATENT DOCUMENTS

| | | |
|---|---|---|
| JP | 2009-537192 A | 10/2009 |
| JP | 4703798 B2 | 6/2011 |

OTHER PUBLICATIONS

Aug. 3, 2016 Office Action issued in Chinese Patent Application No. 201480029628.2.
Nov. 24, 2015 International Preliminary Report on Patentability issued in International Patent Application No. PCT/JP2014/062591.
Aug. 12, 2014 International Search Report issued in International Patent Application No. PCT/JP2014/062591.
Oct. 26, 2017 Office Action issued in European Application No. 14 800 612.5.
Dec. 4, 2017 Office Action issued in Japanese Patent Application No. 2015-518186.

* cited by examiner

PRIOR ART

PRIOR ART

PRIOR ART

STENT

TECHNICAL FIELD

The present invention relates to a stent to be implanted in a somatic lumen such as a blood vessel in order to keep its inner diameter large enough.

BACKGROUND ART

There have been some cases where a stent is implanted in order to push out the lumen walls and keep them in an expanded state for the purpose of preventing restenosis, by means of a device comprising an outer catheter that holds the stent at the tip and an inner piston that pushes forward the stent after the deployment thereof. The stent, as disclosed in Japanese Patent No. JP-B-4703798 (Patent Document 1) for example, includes multiple tubular divided bodies arranged at given distances from each other in the axial direction, and multiple connection sections by which divided bodies axially adjacent to each other are connected with each other. Furthermore, the tubular divided bodies includes multiple linear sections extending in the axial direction arranged along the circumference at nearly equal intervals, and circumferentially adjacent linear sections are connected with each other by turning portions at the end in the axial direction to make zigzag turns in the axial direction so as to be linked in the circumferential direction.

Meanwhile, since an expanded stent is placed in the lumen for a long time, it is required to be stably retained in the initial form after being expanded. That is, the expanded stent requires enough configurational stability against compressive, tensile and torsional forces in order to prevent irregular deformation such as protrusion of the turning portion due to the action of external forces caused by deformation of lumens such as that of expansion, contraction or twisting. At the same time, the expanded stent needs to possess excellent flexibility in a twisting direction to be able to follow the curving deformation of the lumen while keeping an approximate shape of a circular cylinder.

Since the stent described in Patent Document 1 is arranged with many connection sections at equal intervals that are provided on both sides of each linear section in the axial direction, the stent has enough stiffness to achieve configurational stability against compressive, tensile and torsional forces. However, the stent is likely to be insufficient in flexibility in the twisting direction, as shown in FIG. 15, leading to a likelihood of irregular deformation such as that of bending or crushing at a bent portion in response to bending forces.

One option for enhancing the stent's flexibility in the twisting direction is to decrease the number of connection sections 14 as shown in the stent 300 in FIG. 16, while arranging the connection sections 14 provided on both sides of each tubular divided body 12 to have them linked to linear sections 16 different from each other. However, in such a structure, although the flexibility of the stent is enhanced in the twisting direction, configurational stability tends to be insufficient due to reduced stiffness in the axial direction, which posed a likelihood of irresistibility against compressive forces and the like in the axial direction causing irregular plastic deformation as shown in FIG. 17.

BACKGROUND ART DOCUMENT

Patent Document

Patent Document 1: JP-B-4703798

SUMMARY OF THE INVENTION

Problem the Invention Attempts to Solve

The present invention has been developed in view of the above-described matters as the background, and it is an object of the present invention to provide a stent with a novel structure that can achieve both configurational stability against the action of external forces such as compressive, tensile and torsional forces and excellent flexibility in the twisting direction.

Means for Solving the Problem

A first aspect of the present invention provides a stent including: multiple tubular divided bodies each including multiple linear sections extending in an axial direction and being arranged at equal intervals in a circumferential direction, the circumferentially adjacent linear sections being connected with each other by turning portions at their ends in the axial direction so as to make zigzag turns in the axial direction and to be arranged in a tubular shape, and the multiple tubular divided bodies being arranged apart from each other in the axial direction; and connection sections provided between axially adjacent tubular divided bodies and connecting the axially adjacent tubular divided bodies with each other, the stent being characterized in that: three or more connection groups, each including a plurality of the connection sections that are provided close to each other in the circumferential direction between the axially adjacent tubular divided bodies and constitute a connection group, are installed at respective locations at equal intervals in the circumferential direction between the axially adjacent tubular divided bodies, and the connection groups located on axial both sides of each of the tubular divided bodies are installed at respective locations away from each other across at least one turning portion in the circumferential direction.

According to the stent having the structure of the first aspect, the tubular divided bodies that are arranged axially adjacent to each other are connected with each other at three or more locations along the circumference by a connection group comprising multiple connection sections provided circumferentially close to each other. This makes it possible to well establish configurational stability of the stent against external forces either in the axial or circumferential direction, thus preventing irregular deformation such as protrusion of the turning portion toward the outer periphery.

In addition, the connection groups provided on both sides of each tubular divided body in the axial direction are arranged across at least one turning portion in the circumferential direction being placed at locations away from each other. Therefore the stent ensures flexibility against inputs in the twisting direction, and is allowed to have curving deformation while maintaining the tubular shape. As a result, excellent conformability to the curvature of the lumen such as the blood vessel can be achieved where the stent is implanted, thus preventing irregular deformation such as that of bending.

A second aspect of the present invention provides the stent according to the first aspect, wherein the tubular divided bodies axially adjacent to each other are connected with each other by the connection section at the turning portions thereof.

According to the second aspect, by connecting the connection section with the turning portion that straddles over two linear sections circumferentially adjacent to each other, the stent can achieve higher load bearing capacity, and effectively prevents irregular deformation due to the action of external forces. Especially, by providing each connection section in such a way that proximal turning portions of adjacent tubular divided bodies are connected with each other, the length of the connection section can be shortened, thus favorably achieving enhancement of the load bearing capacity and a saving of material to be used and the like.

A third aspect of the present invention provides the stent according to the first or second aspect, wherein the connection groups provided on one side of one of the tubular divided bodies in the axial direction are positioned at middle portions in the circumferential direction between the circumferentially adjacent connection groups on an other side of the one of the tubular divided bodies.

According to the third aspect, the connection groups are arranged in good balance along the circumferential direction, preventing biased stiffness from occurring along the circumference, thus effectively preventing irregular deformation in response to inputs in the axial direction.

A fourth aspect of the present invention provides the stent according to the first to third aspects, wherein at least five of the tubular divided bodies are arranged in the axial direction, of which at least three of the tubular divided bodies located in a middle in the axial direction are connected with each other by the connection groups.

According to the fourth aspect, the tubular divided bodies are connected by the connection groups at least in the middle in the axial direction, thereby achieving configurational stability of the stent against inputs in the axial and circumferential directions as well as flexibility of the stent against inputs in the twisting direction are achieved. If, for example, tubular divided bodies at both ends in the axial direction are connected by more number of the connection groups, high configurational stability can be achieved at the openings of both ends in the axial direction, which are vulnerable to deformation, while maintaining enough flexibility in the middle portion in the axial direction.

A fifth aspect of the present invention provides the stent according to the first to fourth aspects, wherein the connection sections extend linearly all along a length in the axial direction thereof.

According to the fifth aspect, the connection section is restrained from being deformed by inputs in the axial direction, thereby achieving excellent load bearing capacity and configurational stability. Furthermore, since the length of the connection section is shortened, a saving of material to be used for forming the connection section can also be achieved.

A sixth aspect of the present invention provides the stent according to any one of the first to fourth aspects, wherein the connection sections are provided with a deformation buffering part placed inclined against the axial direction.

According to the sixth aspect, since a buffering effect is exerted by deformation and tilting of the deformation buffering part under the action of external forces, concentration of stress can be prevented at the connecting joint between the connection section and the tubular divided body (at both ends of the connection section). Therefore, even if external forces are inputted repeatedly during a long period of implant, excellent durability of the stent can be achieved.

A seventh aspect of the present invention provides the stent according to any one of the first to sixth aspects, wherein the connection sections that constitute at least one connection group are connected with the linear sections circumferentially adjacent to each other.

According to the seventh aspect, each connection group can be formed in a compact manner in the circumferential direction. Therefore, it becomes possible to enhance the configurational stability of the stent by arranging more of the connection groups along the circumference or by composing each connection group with more number of connection sections, and to improve the flexibility of the stent by keeping the intervals between the connection groups large enough in the circumferential direction.

An eighth aspect of the present invention is the stent described in any of the first to seventh aspects, wherein the connection sections that constitute at least one connection group are connected with at least every other linear sections in the circumferential direction.

According to the eighth aspect, flexibility of the stent is favorably achieved against inputs in the twisting direction by providing intervals in the circumferential direction between multiple connection sections that constitute the connection group, thus enabling placement of the stent at bent portions and achieving excellent conformability to the curving deformation or the like at the placement.

A ninth aspect of the present invention provides the stent according to any of the first to eighth aspects, wherein an outer diameter in its expanded state is set at 3 to 12 mm.

According to the ninth aspect, the outer diameter of the stent is made suitable for placing in the blood vessel and can be favorably used for stent grafting, for example.

A tenth aspect of the present invention provides the stent according to any one of the first to ninth aspects, wherein a number of the turning portions on one side of the tubular divided body in the axial direction is set at 12 to 20 along a circumference.

According to the tenth aspect, the linear sections can be formed with a proper width in the stent to be placed in the blood vessel so that both configurational stability against the inputs in the axial and circumferential directions as well as flexibility against inputs in the twisting direction are achieved at the same time.

An eleventh aspect of the present invention provides the stent according to any one of the first to tenth aspects, wherein each of the connection groups is composed of two to three connection sections.

According to the eleventh aspect, the stiffness of each connection group can be set at an appropriate value that would bring both configurational stability and flexibility, while a given number of connection groups can be arranged at equal intervals on the circumference.

Effect of the Invention

According to the present invention, the connection group is composed of multiple connection sections placed circumferentially close to each other, while the tubular divided bodies arranged in the axial direction are connected with each other by three or more connection groups placed at equal intervals on the circumference. Therefore, the configuration of the stent can be stably maintained in response to inputs in the axial and circumferential directions, thus avoiding irregular deformation such as protrusion of the turning portion. Furthermore, the stent relating to the present invention has the connection groups on both sides of the tubular divided body in the axial direction being placed at positions away from each other across at least one turning portion in the circumferential direction. This prevents the linear sections and connection sections from being placed consecutively straddling over multiple tubular divided bodies in the axial direction, thus achieving excellent flexibility against inputs in the twisting direction.

EMBODIMENTS FOR CARRYING OUT THE INVENTION

Embodiments of the present invention will be described below in reference to the drawings.

Figure 1:
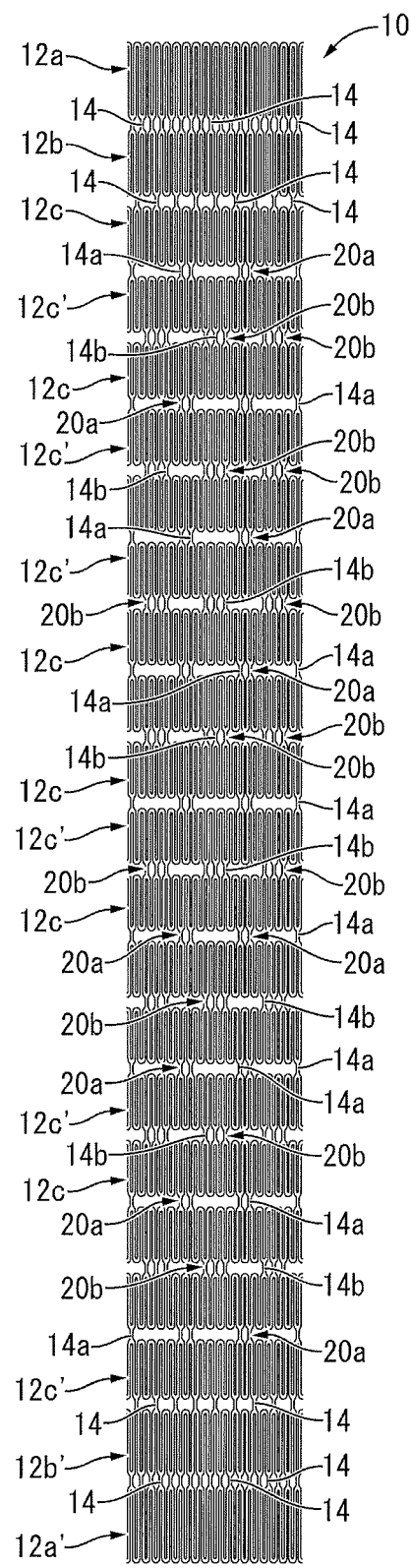
FIG. 1 is a diagram of a stent as a first embodiment of the present invention in a contracted state that is partially developed along the circumference.

FIG. 1 shows a stent 10 as a first embodiment of the present invention in a state of reduced diameter before expansion. The stent 10, in an approximate shape of a circular cylinder as a whole, has a structure where multiple tubular divided bodies 12 are arranged in the axial direction, which are connected with each other by the connection sections 14.

Figure 2:
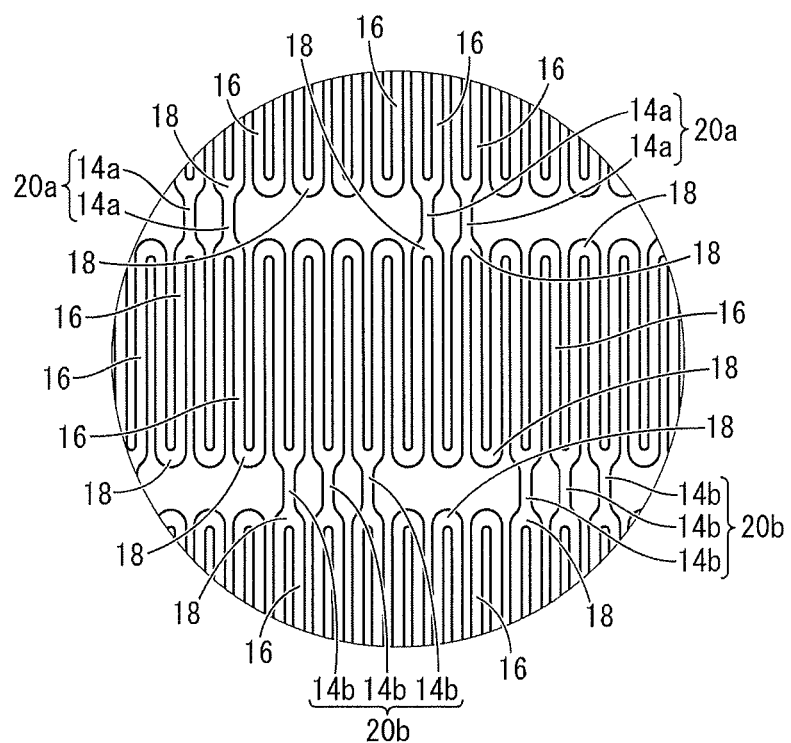
FIG. 2 is a magnified diagram of a key portion of the stent shown in FIG. 1.

In more detail, the tubular divided body 12 is provided with multiple linear sections 16 arranged at equal intervals on the circumference. As shown in FIG. 2, the linear sections 16 are in a form of a narrow and long plate extending almost linearly in the axial direction being arranged in plurality at given intervals in the circumferential direction.

Also, the linear sections 16 adjacent to each other are connected with each other by a turning portion 18 at the end in the axial direction. The turning portion 18, made in a shape of a plate with approximately the same width as the linear section 16, is curving in a semi-circular form. Then, the linear sections 16 continue in the length direction via the turning portions 18 to make zigzag turns in the axial direction so as to extend annularly in the circumferential direction.

Then, twenty-two of the tubular divided bodies 12 are arranged on the same central axis at nearly equal intervals in the axial direction. In the present embodiment, tubular divided bodies 12a and 12a' that are placed at the end of the stent 10 in the axial direction, tubular divided bodies 12b and 12b' that are placed adjacent to the tubular divided bodies 12a and 12a' on the inner side in the axial direction, and nine each of the tubular divided bodies 12c and 12c' that are placed between the tubular divided bodies 12b and 12b' in the axial direction are all arranged in the axial direction. In short, the stent 10 has its both ends in the axial direction composed of the tubular divided bodies 12a, 12a' and 12b, 12b' with its middle portion in the axial direction being composed of nine each of the tubular divided bodies 12c, 12c'. The tubular divided bodies 12a and 12a' are made symmetrical to each other about a plane extending in the transaxial direction, which is also applicable to the tubular divided bodies 12b, 12b' and 12c, 12c'. Also, the tubular divided bodies 12c, 12c' are arranged alternately in the axial direction. The dimensions of the tubular divided bodies 12a, 12a' in the axial direction are made larger than those of the tubular divided bodies 12b, 12b' in the same direction, while the dimensions of the tubular divided bodies 12b, 12b' are made larger than those of the tubular divided bodies 12c, 12c' in the same direction.

The tubular divided bodies 12 arranged as described above are connected with each other between adjacent ones by multiple connection sections 14. The connection section 14 is made in a form of a narrow and long plate as is the linear section 16, which extends linearly in the axial direction all along its length in the present embodiment. Then, both ends of the connection section 14 are integrally connected to either of the tubular divided bodies 12 axially adjacent to each other, which are connected with each other by the connection section 14.

More specifically, the tubular divided bodies 12a, 12a' and 12b, 12b' axially adjacent to each other are connected with each other in the axial direction by having the turning portions 18 of the tubular divided bodies 12a, 12a' and the turning portions 18 of the tubular divided bodies 12b, 12b', both being placed to face in close proximity to each other in the axial direction, all connected by eighteen of the connection sections 14.

Also, the tubular divided bodies 12b, 12b' and the tubular divided bodies 12c, 12c' axially adjacent to each other are connected with each other by having the turning portions 18 of the tubular divided bodies 12b, 12b' and the turning portions 18 of the tubular divided bodies 12, 12c', both being placed in close proximity to each other in the axial direction, connected with each other by nine of the connection sections 14 provided alternately in the circumferential direction.

Under these circumstances, the connection groups 20a and 20b are provided alternately in the axial direction between the tubular divided bodies 12c and 12c' axially adjacent to each other, and the tubular divided bodies 12c and 12c' are connected with each other by the connection group 20. The connection group 20a is composed of two connection sections 14a placed circumferentially close to each other being provided between one end of the tubular divided body 12c in the axial direction (bottom end in FIG. 1) and the other side end of the tubular divided body 12c' (top end in FIG. 1). The connection group 20b is composed of three connection sections 14b that are placed circumferentially close to each other being provided between the other side end of the tubular divided body 12c in the axial direction and one end of the tubular divided body 12c' in the same direction.

Then, the tubular divided bodies 12c and 12c' are connected with each other by having both ends of the connection section 14 constituting each connection group 20 connected to either of the turning portion 18 of the tubular divided body 12c or the turning portion 18 of the tubular divided body 12c'. Furthermore, in the present embodiment, two connection sections 14a constituting the connection group 20a are connected with the turning portions 18 adjacent to each other in the circumferential direction and are connected with the linear sections 16 arranged adjacent to each other in the circumferential direction. Moreover, three of the connection sections 14b constituting the connection group 20b are connected with the turning portions 18 adjacent to each other in the circumferential direction and connected with the linear sections 16 arranged adjacent to each other in the circumferential direction. In the present embodiment, the turning portions 18 of the tubular divided bodies 12c and 12c' placed close to each other in the axial direction are connected with each other by the connection section 14.

Also, on the circumferences of the tubular divided bodies 12c, 12c', three each of the connection groups 20a and 20b are provided at equal intervals in the circumferential direction, and the tubular divided bodies 12c and 12c' are connected with each other by the connection group 20 at three locations on the circumference. Thus, by having three each of the connection groups 20a and 20b provided on the circumference of the tubular divided body 12, four of the turning portions 18 not provided with the connection section 14 are placed between the connection groups 20a in the circumferential direction, while three of the turning portions 18 not provided with the connection section 14 are placed between the connection groups 20b in the circumferential direction.

Additionally, the connection group 20a provided on one side of the tubular divided bodies 12c, 12c' in the axial direction are located at the center in the circumferential direction between the connection groups 20b provided on the other side in the axial direction. This allows the connection section 14a constituting the connection group 20a and the connection section 14b constituting the connection group 20b are placed away from each other on the circumference across at least one turning portion 18. In the present embodiment, the connection sections 14a and 14b are connected with the linear sections 16 that are different from each other via the turning portion 18, and at least one other linear section 16 is arranged between the linear section 16 that is connected with the connection section 14a and the linear section 16 that is connected with the connection section 14b in the circumferential direction.

Then, the tubular divided bodies 12c and 12c' axially adjacent to each other are connected with each other by the connection groups 20a, 20b. This allows the tubular divided bodies 12a, 12a' and 12b, 12b' and 12c, 12c' to be connected in the axial direction to form the stent 10 in a shape of a long cylinder.

Figure 3:
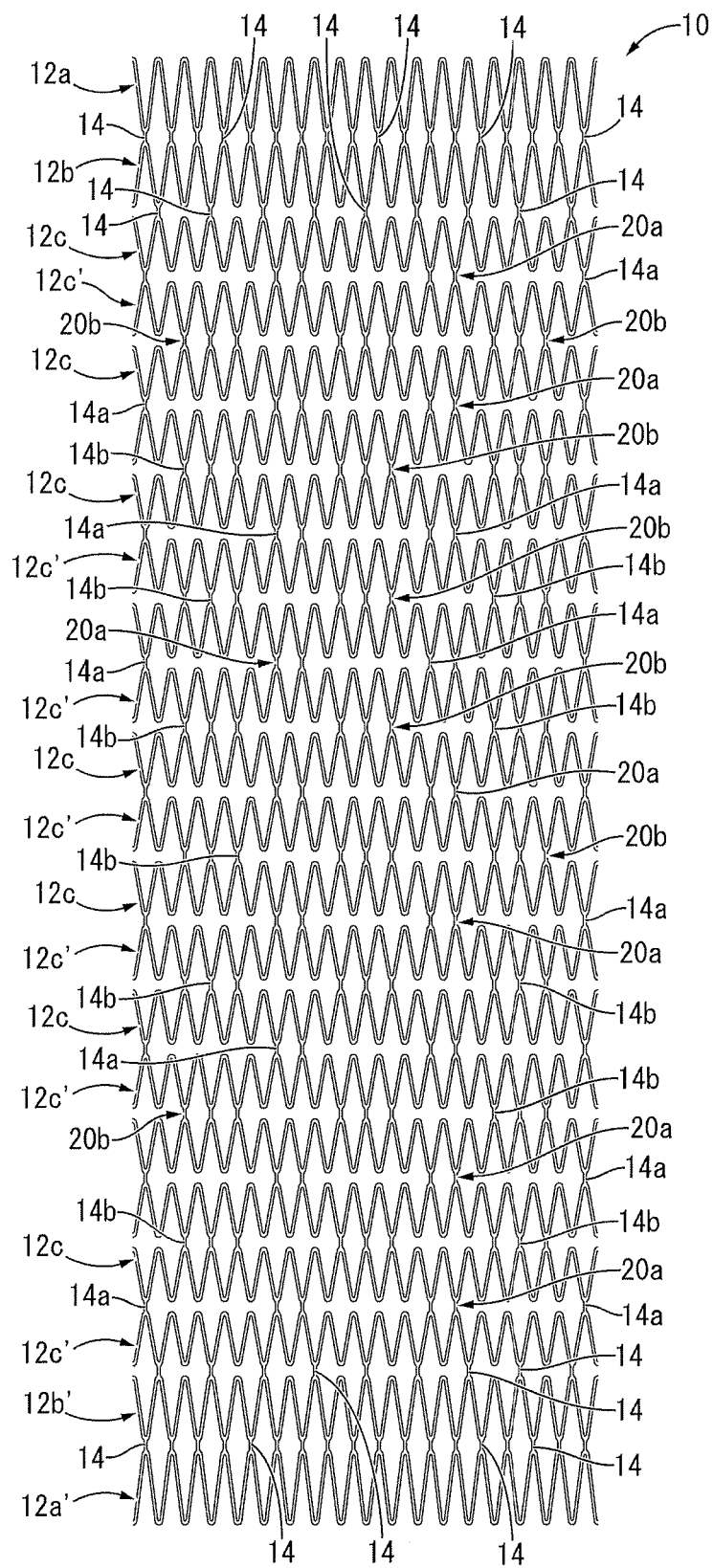
FIG. 3 is a diagram of the stent shown in FIG. 1 in an expanded state that is partially developed along the circumference.

The stent 10 is formed of a material that exerts a shape-memory effect such as Ni—Ti alloy and exhibits super elasticity (pseudo-elasticity) under the body temperature, and by applying heating treatment and the like to the stent under an expanded state (see FIG. 3), the shape in the state of expansion is memorized. This allows the stent 10 to be maintained in a shape under contraction as shown in FIG. 1 by having it inserted into a sheath, not shown, in the contracted state to reach near the stenosis in the lumen, while making it to be a self-expanding stent that automatically restores to an expanded state at the stenosis by having it pushed out of said sheath to free the constraint. The stent 10 described above can be obtained by machining a thin-wall pipe material made of Ni—Ti alloy with laser beam and integrally forming the tubular divided bodies 12a-12c provided with the linear sections 16 and the turning portions 18 with the connection sections 14 that connect them.

Also, the stent 10 preferably has its outer diameter in an expanded state at 3 to 12 mm, and more preferably at 5 to 10 mm, thereby conforming to the inner diameter of the blood vessels at the neck, arms, legs and so forth. In addition, in order to keep the required dimension (width) of the linear section 16 within the outer dimension described above, the number of turning portions 18 on one side of each tubular divided body 12 in the axial direction is preferably between 12 and 20 on the circumference, and eighteen of the turning portions 18 are provided in the present embodiment.

The stent 10 having the structure according to the present embodiment exerts excellent configurational stability under deformation by the action of external forces such as compressive, tensile and torsional forces under a condition of being placed in a stenosis of the blood vessel as a lumen, while having excellent conformability to the curving deformation of the blood vessel.

That is, the tubular divided bodies 12c and 12c' located at the center in the axial direction are connected with each other in the axial direction by the connection groups 20a and 20b, each composed of multiple connection sections 14, and a substantially enough connection area is secured in the circumferential direction. This enables to restrict the amount of deformation in response to the inputs such as compressive and tensile forces in the axial direction, or twisting forces in the circumferential direction to ensure configurational stability, thus avoiding irregular deformation such as protrusion of the turning portion 18 toward the outer periphery. Therefore, failures such as damaging the lumen including blood vessels by the deformed stent 10 can be avoided, thereby ensuring a high safety level.

Furthermore, since three each of the connection groups 20a and 20b are arranged at equal intervals on the circumference, the connection strength of the tubular divided bodies 12c can well be secured. Therefore, stable configuration of the stent can be favorably maintained against external forces applied in the axial and circumferential directions.

In addition, the connection sections 14a, 14b constituting the connection groups 20a, 20b are provided so as to link the turning portions 18 to each other on the proximal sides of the tubular divided bodies 12c and 12c' axially adjacent to each other, and are made in a linear shape extending in the axial direction. This enables to restrain the deformation of the connection sections 14a, 14b, thereby exhibiting a deformation restraining effect that is especially effective against inputs in the axial direction, thus preventing irregular deformation from occurring and achieving excellent configurational stability.

More number of connection sections 14 are provided between the tubular divided bodies 12a, 12a' and the tubular divided bodies 12b, 12b' as well as between the tubular divided bodies 12b, 12b' and the tubular divided bodies 12c, 12c', and the stent 10 is given higher stiffness at both ends than in the middle in the axial direction. This allows the configurational stability of the stent against the action of external forces to be more favorably ensured at both ends in the axial direction.

Also, the connection section 14a constituting the connection group 20a and the connection section 14b constituting the connection group 20b are connected with the linear sections 16 that are different from each other so that the connection sections 14a, 14b constituting the connection groups 20a, 20b, respectively, are not provided at both ends in the axial direction of the same linear section 16. Therefore, elasticity of the stent is achieved to some extent in the axial direction, thereby preventing damages to the stent due to any input in the compressive or tensile direction, whereas the stent undergoes curving deformation in a flexible manner while keeping the tubular shape against inputs in the twisting direction, thus achieving excellent conformability to the curvature of the blood vessels.

Moreover, in the present embodiment, the connection groups 20a are placed in the middle between the connection groups 20b in the circumferential direction. This prevents irregular deformation more effectively under the action of external forces, thus stabilizing deformation configurations.

Figure 4:
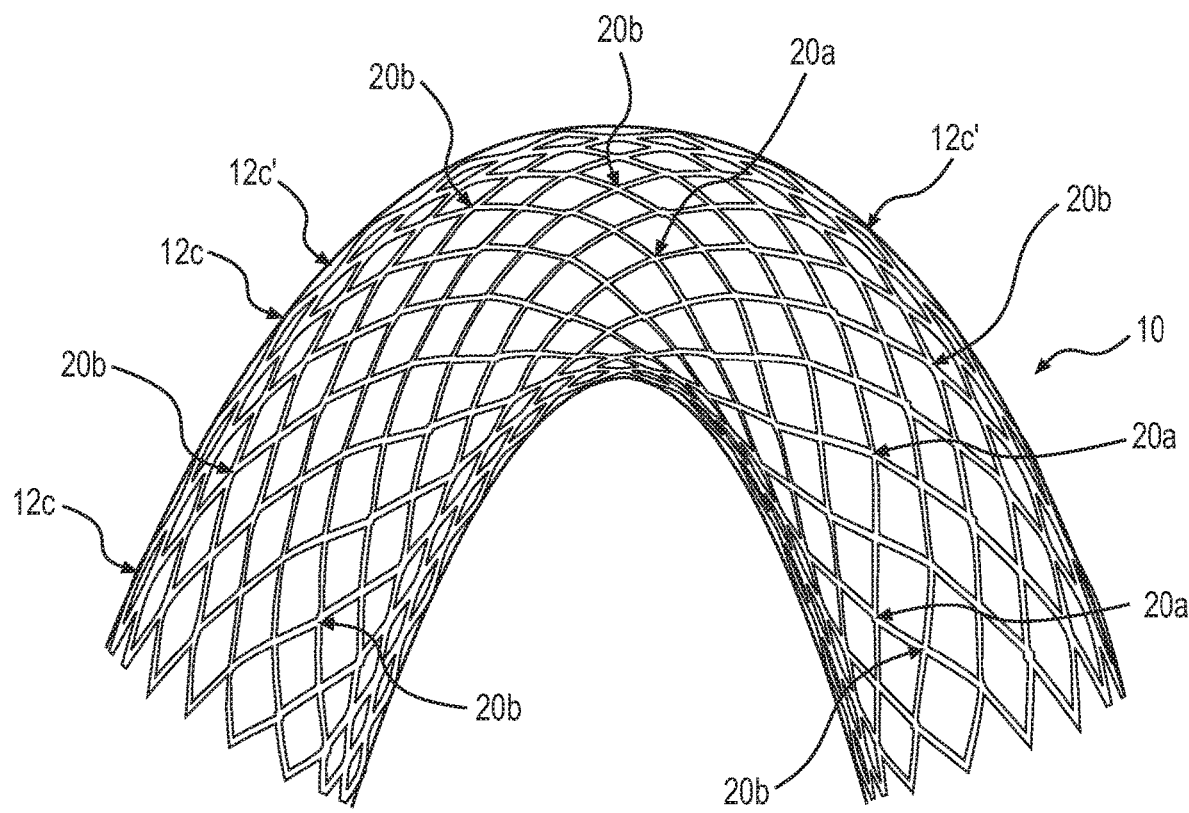
FIG. 4 is a photo of the stent of FIG. 3 with external forces applied in the twisting direction.
Figure 5:
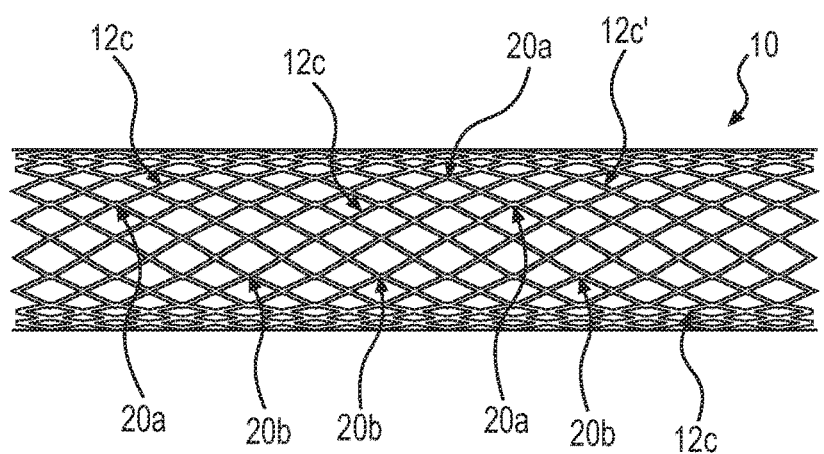
FIG. 5 is a photo of the stent of FIG. 3 with a compressive force applied in the axial direction.

The fact that the stent 10 with the structure according to the present embodiment has both configurational stability against compressive forces in the axial direction and flexibility against external forces in the twisting direction has already been verified by experiments. That is, the stent 10, as shown in FIG. 4, undergoes curving deformation once an external force is applied in the twisting direction, while maintaining the tubular shape without being subject to irregular deformation such as partial bending. Meanwhile, the stent 10, as shown in FIG. 5, stably maintains its tubular shape without causing any irregular deformation such as protrusion of the turning portion 18 toward the outer periphery even when a compressive force is applied in the axial direction.

Figure 13:
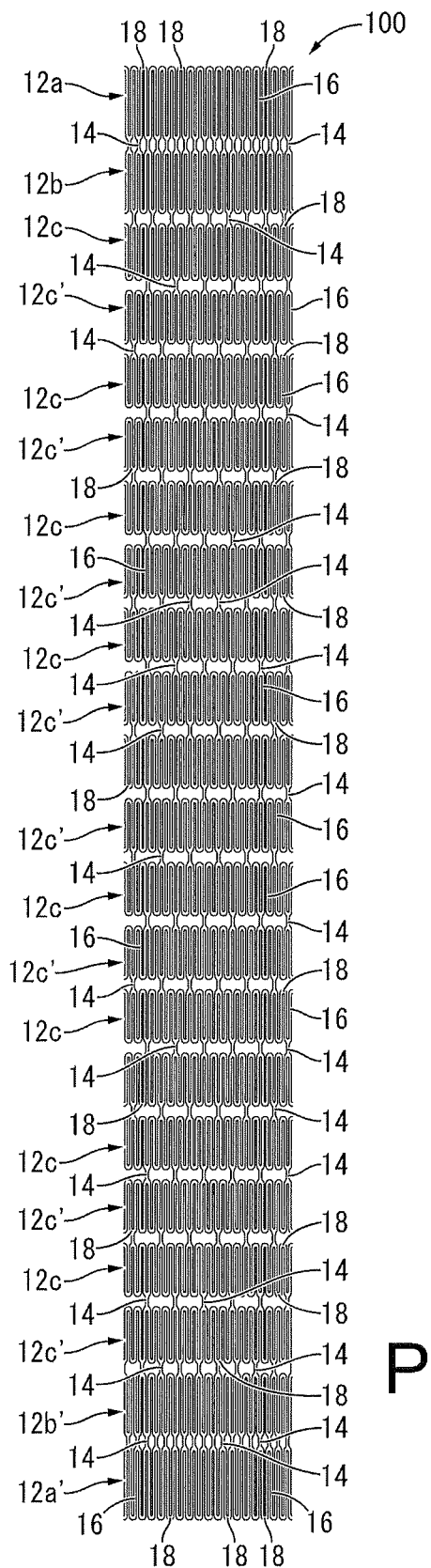
FIG. 13 is a diagram of a stent having a conventional structure in a contracted state that is partially developed along the circumference.
Figure 14:
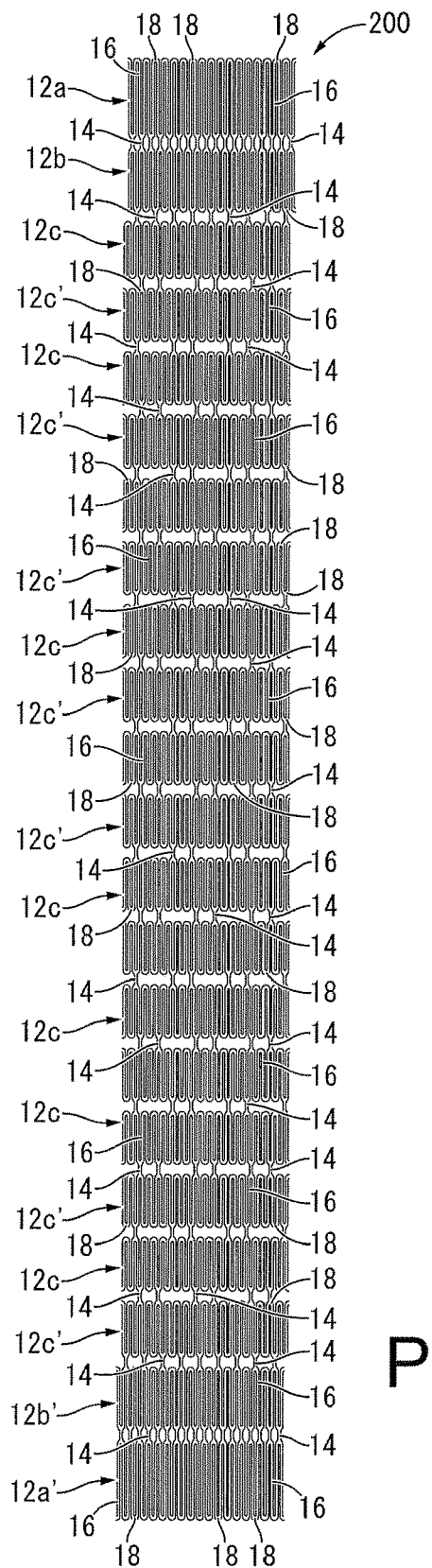
FIG. 14 is a diagram of another stent having a conventional structure in a contracted state that is partially developed along the circumference.
Figure 15:
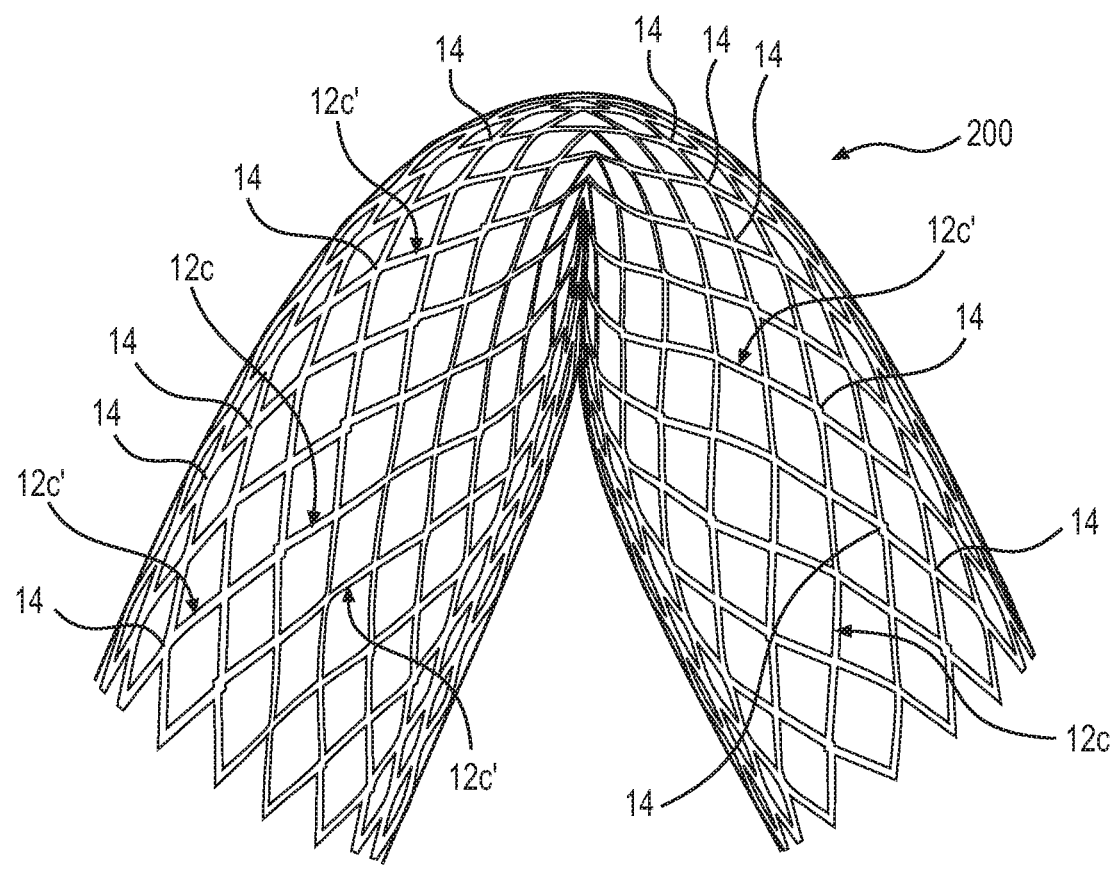
FIG. 15 is a photo of the stent of FIG. 14 with external forces applied in the twisting direction.
Figure 16:
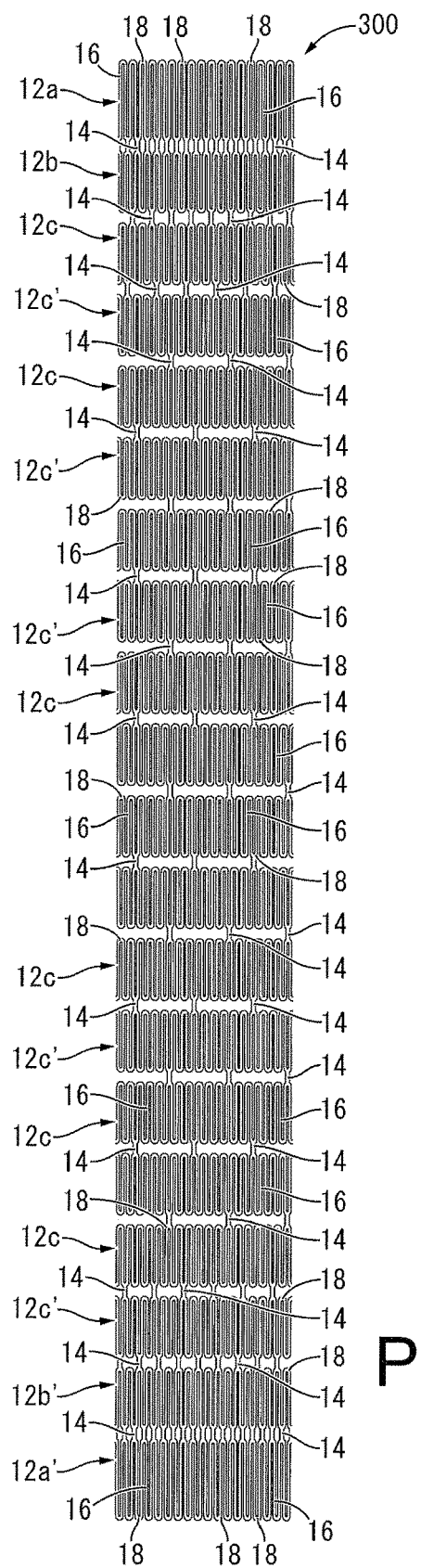
FIG. 16 is a diagram of still another stent having a conventional structure in a contracted state that is partially developed along the circumference.
Figure 17:
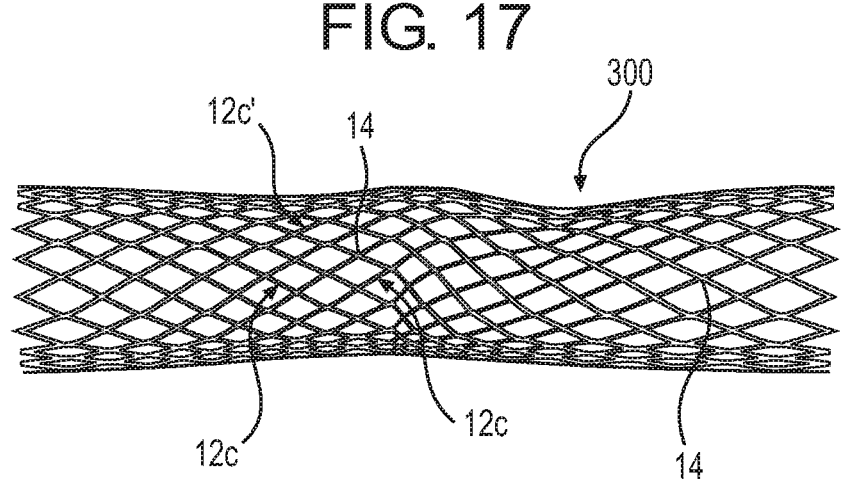
FIG. 17 is a photo of the stent of FIG. 16 with a compressive force applied in the axial direction.

On the contrary, stents 100, 200 with a conventional structure shown in FIGS. 13 and 14 undergo deformation in response to external forces in the twisting direction to develop irregular deformation due to partial bending and the like at the bent portion, as shown in FIG. 15, which makes it difficult to maintain the tubular shape posing a risk such as not being able to stably support the blood vessel walls. Meanwhile, in case of the stent 300 shown in FIG. 16, flexibility against inputs in the twisting direction is ensured, while, once a compressive force is applied in the axial direction, the stent is deformed as if it collapses in the axial direction, as shown in FIG. 17, causing irregular deformation such as protrusion of the turning portion 18 toward the outer periphery. Thus, it was rather difficult for the stents 100, 200 and 300 having a conventional structure to achieve both configurational stability against inputs in the axial direction and flexibility against (conformability to) inputs in the twisting direction.

The stent 100 with a conventional structure (see FIG. 13) has the connection sections 14 that connect the tubular divided bodies 12c and 12c' with each other arranged at equal intervals with two turning portions 18 in between in each interval in the circumferential direction without constituting any connection group. As evident from the structure of the stent 100, by arranging connection sections 14 at equal intervals on the circumference without constituting any connection group, the connection sections 14 need to be provided at smaller intervals in order to ensure configurational stability against inputs in the axial direction, thus reducing flexibility against inputs in the twisting direction.

Also, the stent 200 with a conventional structure (see FIG. 14) has some of the connection sections 14 that connect the tubular divided bodies 12c and 12c' with each other connected to both sides of the same linear section 16 in the axial direction. This ensures configurational stability against inputs in the axial direction, while making it difficult to obtain flexibility against inputs in the twisting direction.

Additionally, the stent 300 with a conventional structure (see FIG. 16) has less number of connection sections 14 that connect the tubular divided bodies 12c and 12c' with each other than the stent 10, and those connection sections 14 are arranged in equal intervals in the circumferential direction with five of the turning portions 18 in between in each interval. This improves flexibility against inputs in the twisting direction, while making it easier to induce irregular deformation due to insufficient configurational stability against inputs in the axial direction.

Figure 6:
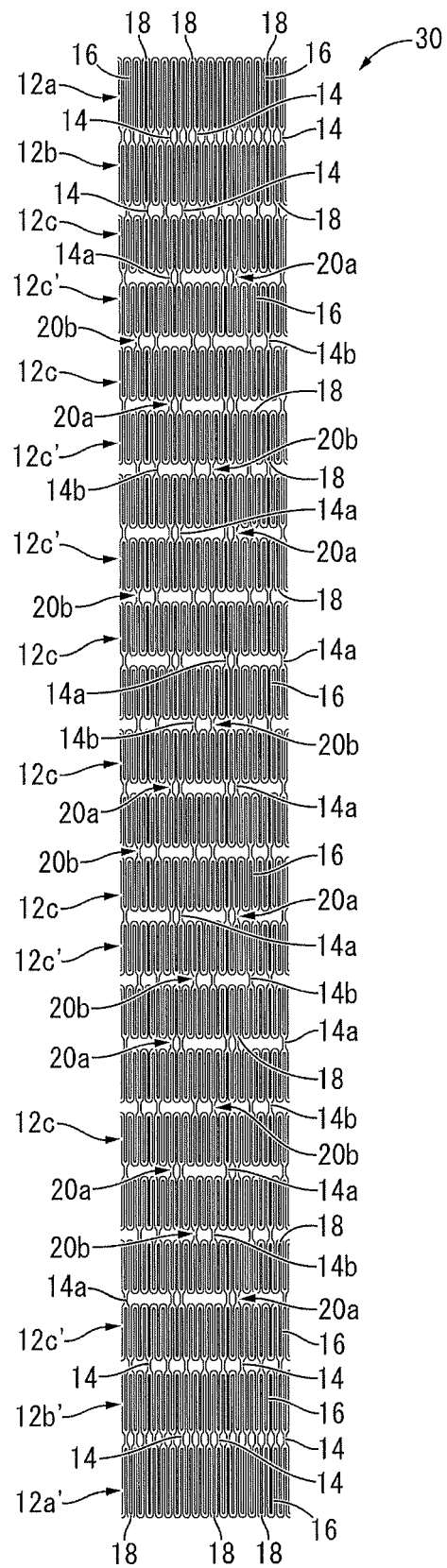
FIG. 6 is a diagram of a stent as a second embodiment of the present invention in a contracted state that is partially developed along the circumference.

FIG. 6 shows a stent 30 as a second embodiment of the present invention in a state of reduced diameter in a development view. In the following paragraphs, descriptions of substantially the same members and portions as those of the first embodiment will be omitted by allocating the same reference numerals in the figures.

In more detail, the stent 30 has the connection groups 20b that connect the tubular divided bodies 12c and 12c' with each other composed of two connection sections 14b, while having the two connection sections 14b constituting the connection group 20b connected with the turning portions 18 arranged in the circumferential direction with one turning portion 18 in between, and connected with linear sections 16 on both sides in the circumferential direction with two linear sections 16 in between.

The stent 30 with the structure described above can also achieve both configurational stability against inputs in the axial and circumferential directions and flexibility against inputs in the twisting direction as is the case with the stent 10 of the first embodiment.

In addition, according to the stent 30 relating to the present embodiment, since the connection section 14b in the middle in the circumferential direction is omitted from the connection group 20b, flexibility in the twisting direction is further enhanced, thus achieving excellent conformability to the curving deformation of blood vessels or the like.

Figure 7:
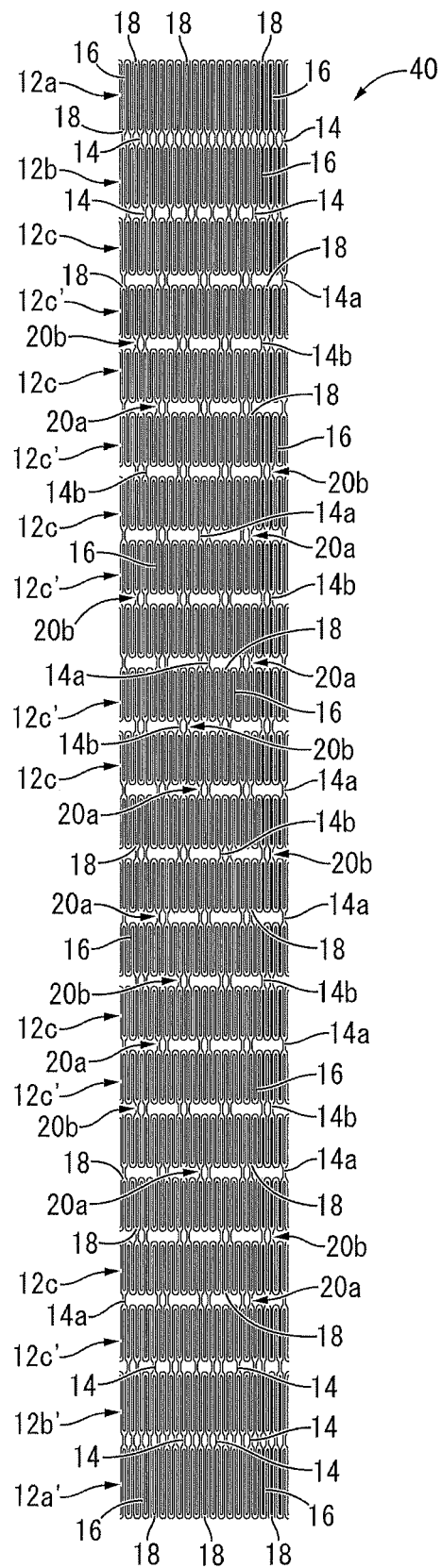
FIG. 7 is a diagram of a stent as a third embodiment of the present invention in a contracted state that is partially developed along the circumference.

FIG. 7 shows a stent 40 as a third embodiment of the present invention. The stent 40 is provided with forty of the linear sections 16 in each row as well as twenty of the turning portions 18 that connect those linear sections 16 on one side in the axial direction.

Also, the stent 40 is provided with the connection groups 20 that connect the tubular divided bodies 12c and 12c' with each other. The connection group 20, as is the case with the connection group 20a of the first embodiment, is composed of two of the connection sections 14 that are connected with turning portions 18 circumferentially adjacent to each other, and four of the connection groups 20 are arranged at equal intervals with three turning portions 18 in between in each interval. The stent 40 of the present embodiment has the connection group 20a provided on one side of the tubular divided body 12c in the axial direction and the connection group 20b provided on the other side in the axial direction in structures identical to each other, and each connection group 20a is arranged to be placed in the middle of two connection groups 20b in the circumferential direction.

Additionally, the connection sections 14 that connect the tubular divided bodies 12b, 12b' and 12c, 12c' are arranged in such a way that a pair of the connection sections 14 connected with the turning portions 18 circumferentially adjacent to each other and one connection section 14 placed across one turning portion 18 from the pair of connection sections 14 in the circumferential direction are repeatedly arranged in the circumferential direction. In other words, the pair of connection sections 14 connected with the turning portions 18 circumferentially adjacent to each other are arranged with three of the turning portions 18 in between in the circumferential direction, while one connection section 14 is provided at the turning portion 18 located in between each pair of connection sections 14 in the circumferential direction.

The stent 40 with the structure described above also realizes configurational stability against inputs in the axial and circumferential directions, as do the stents 10 and 30 of the first and second embodiments, respectively, thus favorably ensuring safety in case of deformation of the stent 10, while flexibility against inputs in the twisting direction is secured, thus achieving excellent conformability to curving deformation of blood vessels and the like.

Also, in the stent 40 of the present embodiment, four each of the connection groups 20a, 20b are placed along the circumference enhancing the load bearing capacity in response to inputs in the axial and circumferential directions, while configurational stability is maintained during deformation to prevent irregular deformation such as protrusion of the turning portion 18 toward the outer periphery, thus further improving safety in case of excessive inputs.

Figure 8:
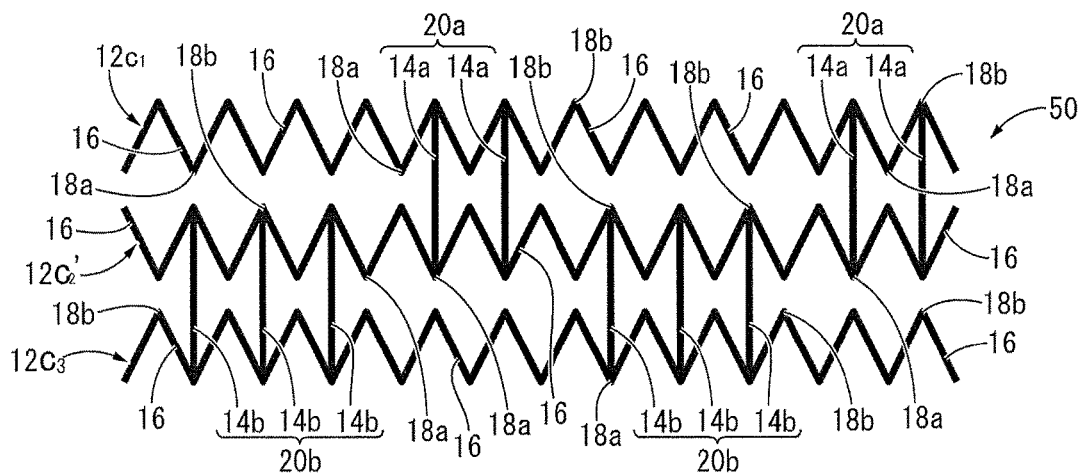
FIG. 8 is a magnified diagram of a key portion of a stent as a fourth embodiment of the present invention in an expanded state that is partially developed along the circumference.

FIG. 8 shows a stent 50 as a fourth embodiment of the present invention in a schematic diagram with part of the central portion in the axial direction extracted and magnified. The stent 50 of the present embodiment has the tubular divided bodies 12c and 12c' arranged alternately in the axial direction and connected with each other in the axial direction by the connection groups 20a and 20b. For better understanding, the tubular divided body located at the top is named $12c_1$, the one in the middle $12c'_2$, and the one at the bottom $12c_3$ in FIG. 8, and the same numbering will be applied to the stents shown in FIGS. 9 to 12.

The two of the connection sections 14a constituting the connection group 20a are provided so as to connect the turning portion 18b located on one side of the tubular divided body $12c_1$ in the axial direction (top side in FIG. 8) and the turning portion 18a located on the other side of the tubular divided body $12c'_2$ in the axial direction (bottom side in FIG. 8) with each other. Meanwhile, three of the connection sections 14b constituting the connection group 20b are provided so as to connect the turning portion 18b located on one side of the tubular divided body $12c'_2$ in the axial direction and the turning portion 18a located on the other side of the tubular divided body $12c_3$ in the axial direction with each other. In summary, the connection sections 14 of the present embodiment are provided to link the turning portions 18 located on distal sides in the axial direction, not on proximal sides, so that the dimension of the connection sections is made larger.

The stent 50 with the structure according to the present embodiment also exerts the same effects as those of the stent shown in each previous embodiment. In addition, setting the length of the connection section 14 large enough makes it possible to improve the flexibility of the stent more effectively in the twisting direction.

Figure 9:
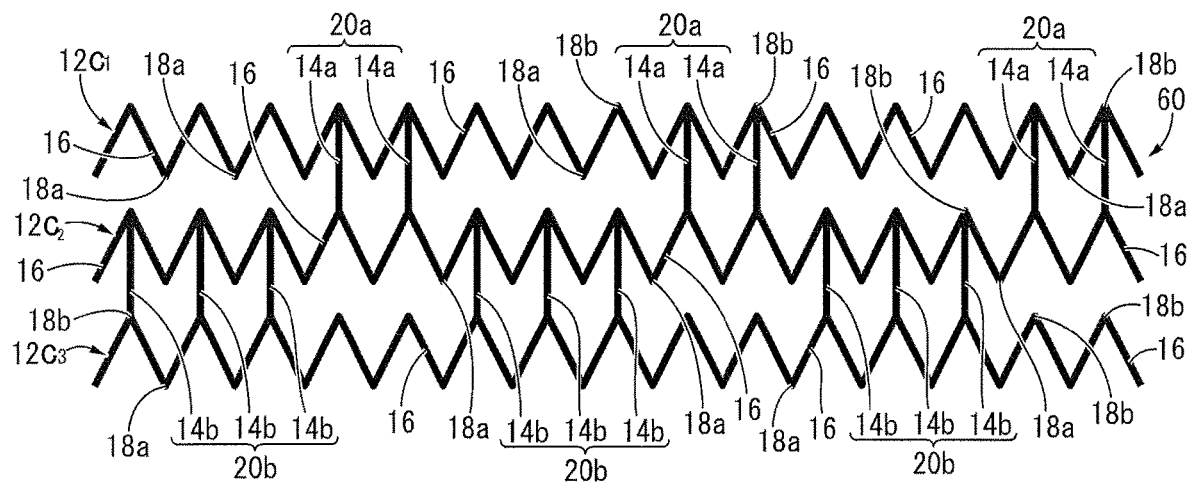
FIG. 9 is a magnified diagram of a key portion of a stent as a fifth embodiment of the present invention in an expanded state that is partially developed along the circumference.

FIG. 9 shows a stent 60 as a fifth aspect of the present invention in a schematic diagram with part of the central portion in the axial direction extracted and magnified. The stent 60 of the present embodiment has the tubular divided bodies 12c arranged at given intervals in the axial direction, and between these tubular divided bodies 12c in the axial direction, the connection groups 20a and 20b are alternately arranged.

Two of the connection sections 14a constituting the connection group 20a are provided so as to connect the turning portion 18b of the tubular divided body $12c_1$ and the turning portion 18b of the tubular divided body $12c_2$ with each other. Meanwhile, three connection sections 14b that constitute the connection group 20b are provided so as to connect the turning portion 18b of the tubular divided body $12c_2$ and the turning portion 18b of the tubular divided body $12c_3$ with each other. In summary, the connection section 14 of the present embodiment is provided to link the turning portions 18 located on distal sides and the turning portions 18 located on proximal sides in the axial direction, and the length of the connection section 14 is set in the middle between the structure shown in the first to third embodiments and the structure shown in the fourth embodiment.

The stent 60 with the structure according to the present embodiment also exerts the same effects as those of the stent shown in each previous embodiment. In addition, setting the length of the connection section 14 in the middle makes it possible to effectively obtain load bearing capacity and configurational stability in the axial and circumferential directions as well as flexibility in the twisting direction.

Figure 10:
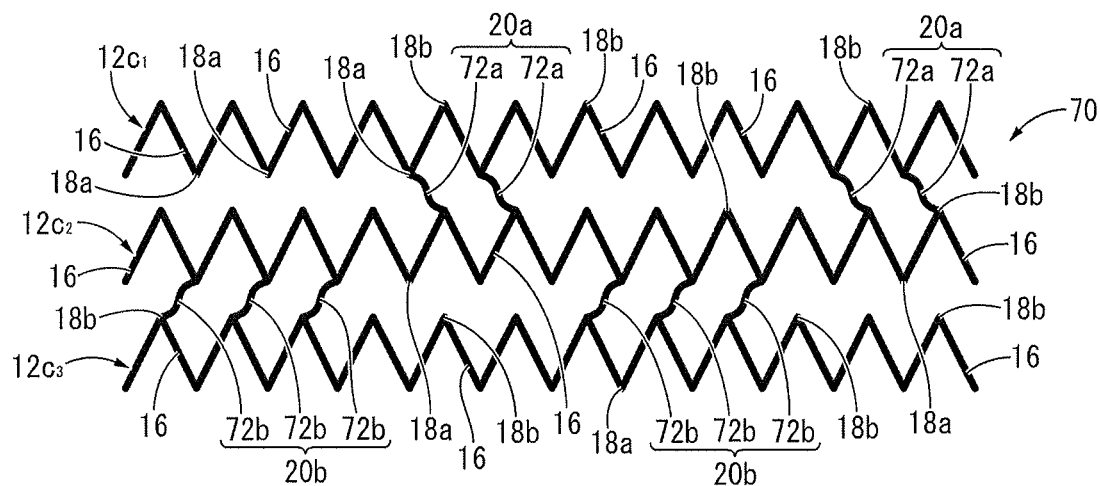
FIG. 10 is a magnified diagram of a key portion of a stent as a sixth embodiment of the present invention in an expanded state that is partially developed along the circumference.

FIG. 10 shows a stent 70 as a sixth embodiment of the present invention in a schematic diagram with part of the central portion in the axial direction extracted and magnified. In the stent 70 of the present embodiment, a plurality of the tubular divided bodies 12c arranged at given intervals in the axial direction are connected with each other by the connection group 20a composed of two connection sections 72a and the connection group 20b composed of three connection sections 72b.

The connection section 72a, in a narrow and long shape curving in a reverse S as a whole, connects with each other the turning portion 18a of the tubular divided body $12c_1$ and the turning portion 18b of the tubular divided body $12c_2$ placed close to each other in the axial direction.

The connection section 72b, in a narrow and long shape curving in a S as a whole, connects with each other the turning portion 18a of the tubular divided body $12c_2$ and the turning portion 18b of the tubular divided body $12c_3$ placed close to each other in the axial direction. The connection sections 72a and 72b are each in a continuously curved shape as a whole being inclined against the axial direction, and their deformation buffering parts are composed of the entirety of the connection sections 72a and 72b.

The stent 70 with the structure according to the present embodiment also exerts the same effects as those of the stent shown in each previous embodiment. In addition, since the connection section 72 is provided with the deformation buffering part, deformation in the axial direction is more likely to be elastically allowed, thus favorably preventing the stent 70 from being damaged under the action of external forces.

Figure 11:
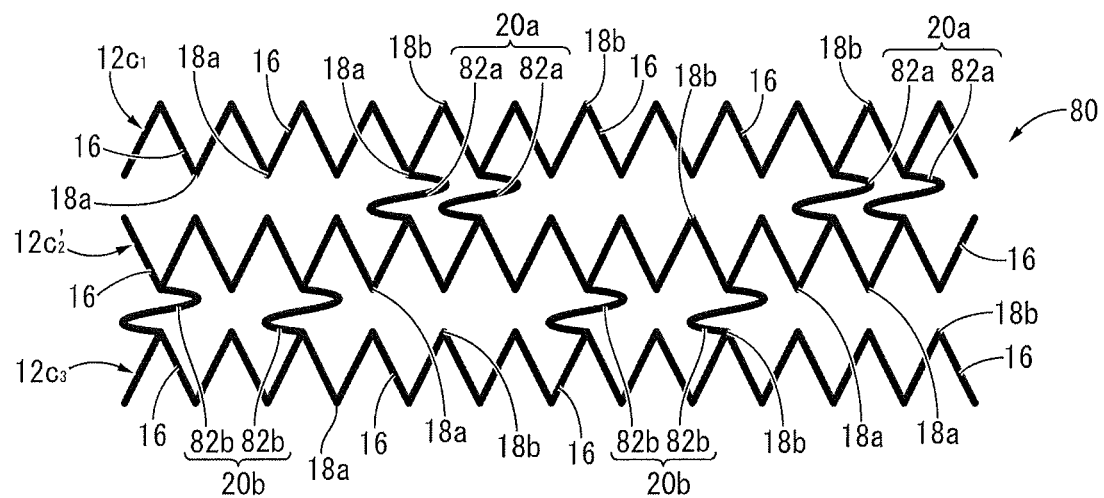
FIG. 11 is a magnified diagram of a key portion of a stent as a seventh embodiment of the present invention in an expanded state that is partially developed along the circumference.

FIG. 11 shows a stent 80 as a seventh aspect of the present invention in a schematic diagram with part of the central portion in the axial direction extracted and magnified. In the stent 80 of the present embodiment, the tubular divided bodies 12c and 12c' arranged alternately in the axial direction are connected with each other in the axial direction by the connection groups 20a and 20b.

A connection section 82 constituting the connection groups 20a, 20b extends in a significant curve forming a Z-shape, and the entire curvature is made to be a deformation buffering part that extends inclined against the axial direction. Then, the connection group 20a is composed of two connection sections 82a that connect with each other the turning portion 18a of the tubular divided body $12c_1$ and the turning portion 18b of the tubular divided body $12c'_2$ closely placed to each other, while the connection group 20b is composed of two connection sections 82b that connect with each other the turning portion 18a of the tubular divided body $12c'_2$ and the turning portion 18b of the tubular divided body $12c_3$ closely placed to each other. In the present embodiment, the connection group 20a is composed of two connection sections 82a connected to two turning portions 18 placed circumferentially adjacent to each other, while the connection group 20b is composed of two connection sections 82b connected to two turning portions 18 placed across another turning portion 18 in the circumferential direction.

The stent 80 with the structure according to the present embodiment also exerts the same effects as those of the stent shown in each previous embodiment. In addition, since the connection section 82 in a curved shape being inclined against the axial direction exhibits some elasticity in response to inputs in the axial and circumferential directions, durability and configurational stability of the stent can be achieved to a higher degree. Furthermore, the connection section 82 is curved more significantly than the connection section 72 of the stent 70 shown as a sixth embodiment, the above-mentioned elasticity is exerted more effectively, thus improving durability and configurational stability of the stent.

Figure 12:
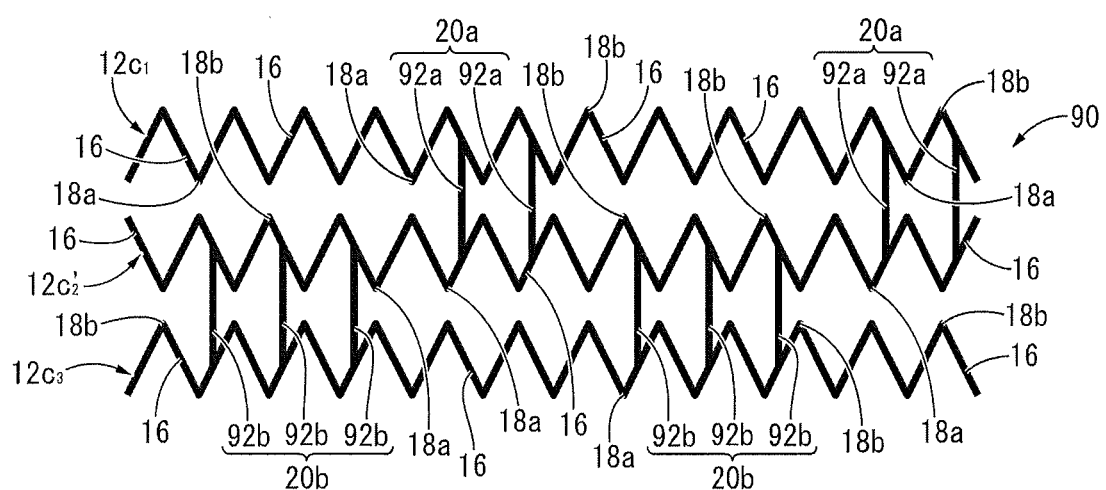
FIG. 12 is a magnified diagram of a key portion of a stent as an eighth embodiment of the present invention in an expanded state that is partially developed along the circumference.

FIG. 12 shows a stent 90 as an eighth aspect of the present invention in a schematic diagram with part of the central portion in the axial direction extracted and magnified. In the stent 90 of the present embodiment, the tubular divided bodies 12c and 12c' alternately arranged in the axial direction are connected with each other in the axial direction by the connection groups 20a and 20b.

The connection section 92 constituting the connection groups 20a, 20b extends linearly in the axial direction having its both ends connected to the middle portion in the length direction of the linear sections 16 arranged diagonally against the axial direction, connecting those linear sections 16 with each other. The connection group 20a is composed of two connection sections 92a being provided between the tubular divided bodies $12c_1$ and $12c'_2$ in the axial direction, while the connection group 20b is composed of three connection sections 92b being provided between the tubular divided bodies $12c'_2$ and $12c_3$ in the axial direction.

According to the stent 90 with the structure of the present embodiment, the length of the connection section 92 can be made large enough, enabling to achieve both load bearing capacity and configurational stability in the axial and circumferential directions as well as flexibility in the twisting direction each in an effective manner. In addition, by properly setting the connection position of the linear section 16 to the connection section 92 in the length direction, it becomes possible to adjust the length of the connection section 92.

Embodiments of the present invention have been described above, but the present invention is not limited by those descriptions. For example, the connection section 14 can be provided so as to connect the turning portion 18 and the middle portion of the linear section 16 with each other.

Also, the specific configuration of the connection section 14 is not limited to those shown in the embodiments described above. For example, connection sections in a sideway U-shape or V-shape that make convex on one side in the circumferential direction can also be adopted.

Additionally, in case of providing the connection section with a deformation buffering part, the entire connection section can be made into a deformation buffering part, but curved and/or inclined portions can be partially provided in the middle of the connection section in the length direction, for example, and the deformation buffering part can be composed of those curved and/or inclined portions. In short, if at least part of the connection section is inclined against the axial direction, the deformation buffering part can be composed of the inclined portion.

Furthermore, the connection groups 20a, 20b provided on both sides of the tubular divided body 12 in the axial direction are preferably placed in the middle of each other's interval in the circumferential direction, but also can be provided off such middle positions in the circumferential direction.

Moreover, the number of the tubular divided bodies 12 arranged in the axial direction is not particularly limited and can be set arbitrarily depending on the lesion where the stent is applied and the length of stenosis and the like. Furthermore, the ratio of numbers of the tubular divided body 12a to the tubular divided body 12b shown in the previous embodiments is just an example and is not particularly limited. Moreover, it is possible to omit the tubular divided bodies 12a, 12a' as well as 12b, 12b', and the entire stent can be composed of the tubular divided bodies 12c and/or 12c'.

Also, the stent 10 as a whole may have a constant outer diameter, but can be made to exert a positioning function in the axial direction in the lumen by means of making the end tip in the axial direction in a tapered shape that gradually increases its diameter outward in the axial direction.

Additionally, in the previous embodiments, a self-expansion type stent with shape-memory effect was exemplified, but the present invention is also applicable to a balloon-expandable type stent that is pushed out to be dilated by means of inflating a balloon that has been pre-inserted. In case of applying the present invention to the balloon-expandable type stent, the materials to form the stent are not limited to those capable of shape-memory behavior, but for example, the stent can be formed of other materials such as medical stainless steel.

KEYS TO SYMBOLS 10, 30, 40, 50, 60, 70, 80, 90: Stent; 12: tubular divided body; 14, 72, 82, 92: Connection section; 16: Linear section; 18: Turning portion; 20: Connection group

The invention claimed is:

1. A stent comprising:
   multiple tubular divided bodies each consisting of multiple circumferentially adjacent linear sections extending in an axial direction and being arranged at equal intervals in a circumferential direction, the circumferentially adjacent linear sections being connected with each other by turning portions at their ends in the axial direction so as to form a structure continuing in a length direction via the turning portions, making zigzag turns in the axial direction and being arranged in a tubular shape, and the multiple tubular divided bodies being arranged apart from each other in the axial direction; and connection sections provided between axially adjacent tubular divided bodies and connecting the axially adjacent tubular divided bodies with each other, wherein three or more connection groups, each including a plurality of the connection sections that are (i) provided between the axially adjacent tubular divided bodies, (ii) circumferentially adjacent and (iii) constitute a connection group, are installed at respective locations at equal intervals in the circumferential direction between the axially adjacent tubular divided bodies, the connection groups located on axial both sides of each of the tubular divided bodies are installed at respective locations away from each other across at least one turning portion in the circumferential direction, and each of the turning portions of each of the tubular divided bodies connects to one or less of the connection sections so that a plurality of the turning portions of each of the tubular divided bodies are connected by each of the connection groups.

2. The stent according to claim 1, wherein the tubular divided bodies axially adjacent to each other are connected with each other by the connection sections at the turning portions thereof.

3. The stent according to claim 1, wherein the connection groups provided on one side of one of the tubular divided bodies in the axial direction are positioned at middle portions in the circumferential direction between the circumferentially adjacent connection groups on another side of the one of the tubular divided bodies.

4. The stent according to claim 1, wherein at least five of the tubular divided bodies are arranged in the axial direction, of which at least three of the tubular divided bodies located in a middle in the axial direction are connected with each other by the connection groups.

5. The stent according to claim 1, wherein the connection sections extend linearly all along a length in the axial direction thereof.

6. The stent according to claim 1, wherein the connection sections are provided with a deformation buffering part placed inclined against the axial direction.

7. The stent according to claim 1, wherein the connection sections that constitute at least one connection group are connected with the circumferentially adjacent linear sections.

8. The stent according to claim 1, wherein the connection sections that constitute at least one connection group are connected with at least every other linear section in the circumferential direction.

9. The stent according to claim 1, wherein an outer diameter of the stent in an expanded state is set at 3 to 12 mm.

10. The stent according to claim 1, wherein a number of the turning portions on one side of the tubular divided body in the axial direction is set at 12 to 20 along a circumference.

11. The stent according to claim 1, wherein each of the connection groups is composed of two to three connection sections.

12. The stent according to claim 1, wherein each turning portion of each tubular divided body is spaced apart from adjacent turning portions of the respective tubular divided body in the circumferential direction of the tubular divided body.

* * * * *